US006767722B1

(12) United States Patent
Springer et al.

(10) Patent No.: US 6,767,722 B1
(45) Date of Patent: *Jul. 27, 2004

(54) ANALOGS OF HUMAN BASIC FIBROBLAST GROWTH FACTOR MUTATED AT ONE OR MORE OF THE POSITIONS GLUTAMATE 89, ASPARTATE 101 OR LEUCINE 137

(75) Inventors: Barry A. Springer, Wilmington, DE (US); Michael W. Pantoliano, Avondale, PA (US); Celia M. Sharp, Doylestown, PA (US)

(73) Assignee: 3-Dimensional Pharmaceuticals, Inc., Exton, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 51 days.

This patent is subject to a terminal disclaimer.

(21) Appl. No.: 09/722,495

(22) Filed: Nov. 28, 2000

Related U.S. Application Data (63) Continuation of application No. 09/220,077, filed on Dec. 23, 1998, now Pat. No. 6,274,712.
(60) Provisional application No. 60/068,667, filed on Dec. 23, 1997.

(51) Int. Cl.⁷ .................. C12N 15/12; C12N 15/63; C12N 1/21; A61K 38/18; C07K 14/50
(52) U.S. Cl. .................. 435/69.4; 243/320.1; 243/325; 536/23.5; 514/12; 530/399; 930/10
(58) Field of Search .................. 530/399; 435/69.4, 435/320.1; 514/2, 12; 930/10

(56) References Cited

U.S. PATENT DOCUMENTS

| | | | |
|---|---|---|---|
| 4,785,079 | A | 11/1988 | Gospodarowicz et al. |
| 4,902,782 | A | 2/1990 | Gospodarowicz et al. |
| 4,956,455 | A | 9/1990 | Esch et al. |
| 4,994,559 | A | 2/1991 | Moscatelli et al. |
| 5,026,839 | A | 6/1991 | Moscatelli et al. |
| 5,130,418 | A | 7/1992 | Thompson |
| 5,132,408 | A | 7/1992 | Baird et al. |
| 5,136,025 | A | 8/1992 | Scheuermann et al. |
| 5,143,829 | A | 9/1992 | Thompson et al. |
| 5,155,214 | A | 10/1992 | Baird et al. |
| 5,191,067 | A | 3/1993 | Lappi et al. |
| 5,206,354 | A | 4/1993 | Seddon et al. |
| 5,217,954 | A | 6/1993 | Foster et al. |
| 5,252,718 | A | 10/1993 | Baird et al. |
| 5,302,702 | A | 4/1994 | Seddon et al. |
| 5,310,883 | A | 5/1994 | Seddon et al. |
| 5,331,095 | A | 7/1994 | Shadle et al. |
| 5,332,804 | A | 7/1994 | Florkiewicz et al. |
| 5,348,863 | A | 9/1994 | Monsan et al. |
| 5,350,836 | A | 9/1994 | Kopchick et al. |
| 5,352,589 | A | 10/1994 | Bergonzoni et al. |
| 5,360,896 | A | 11/1994 | Senoo et al. |
| 5,371,206 | A | 12/1994 | Seddon et al. |
| 5,387,673 | A | 2/1995 | Seddon et al. |
| 5,439,818 | A | 8/1995 | Fiddes et al. |
| 5,459,250 | A | 10/1995 | Basilico et al. |
| 5,464,774 | A | 11/1995 | Baird et al. |
| 5,478,804 | A | 12/1995 | Calabresi et al. |
| 5,482,929 | A | 1/1996 | Fukunaga et al. |
| 5,491,220 | A | 2/1996 | Seddon et al. |
| 5,514,566 | A | 5/1996 | Fiddes et al. |
| 5,514,652 | A | 5/1996 | Watanuki et al. |
| 5,576,288 | A | 11/1996 | Lappi et al. |
| 5,604,293 | A | 2/1997 | Fiddes et al. |
| 5,612,211 | A | 3/1997 | Wilson et al. |
| 5,614,496 | A | 3/1997 | Dunstan et al. |
| 5,656,598 | A | 8/1997 | Dunstan et al. |
| 6,451,561 | B1 * | 9/2002 | Wells et al. |

FOREIGN PATENT DOCUMENTS

| EP | 0 237 966 A2 | 9/1987 |
|---|---|---|
| EP | 0 281 822 A2 | 9/1988 |
| EP | 0 363 675 A1 | 4/1990 |
| EP | 0 420 222 A1 | 4/1991 |
| EP | 0 510 662 A1 | 10/1992 |
| EP | 0 281 822 B1 | 7/1994 |
| WO | WO 90/02800 | 3/1990 |
| WO | WO 91/09126 | 6/1991 |
| WO | WO 91/14785 | 10/1991 |
| WO | WO 95/08630 | 3/1995 |
| WO | WO 96/22369 | 7/1996 |

OTHER PUBLICATIONS

Ago, H. et al., "Crystal Structure of Basic Fibroblast Growth Factor at 1.6 A Resolution," *J. Biochem.* 110:360–363, Japanese Biochemical Society (1991).

Arakawa, T. et al., "Characterization of a Cysteine–Free Analog of Recombinant Human Basic Fibroblast Growth Factor," *Biochem. Biophys. Comm.* 161(1):335–341, Academic Press, Inc. (1989).

Arakawa, T. et al., "The Importance of Arg40 and 45 in the Mitogenic Activity and Structural Stability of Basic Fibroblast Growth Factor: Effects of Acidic Amino Acid Substitutions," *J. Prot. Chem.* 14(5):263–274, Plenum Publishing Corporation (1995).

Basilico, C. and Moscatelli, D., "The FGF Family of Growth Factors and Oncogenes," *Adv Canc. Res.* 59:115–165, Academic Press, Inc. (1992).

(List continued on next page.)

Primary Examiner—Christine J. Saoud
(74) Attorney, Agent, or Firm—Woodcock Washburn LLP

(57) ABSTRACT

The present invention relates to muteins of human basic fibroblast growth factor with superagonist properties. Both protein and the respective encoding nucleic acid species are disclosed. The invention also embodies vectors and host cells for the propagation of said nucleic acid sequences and the production of said muteins. Also disclosed is a method for stimulating cell division.

29 Claims, 2 Drawing Sheets

OTHER PUBLICATIONS

Blaber, M. et al., "X–ray Crystal Structure of Human Acidic Fibroblast Growth Factor," *Biochemistry 35(7)*:2086–2094, American Chemical Society (Feb. 1996).

Bowie, J. et al., "Deciphering the Message in Protein Sequences: Tolerance to Amino Acid Substitutions," *Science 247*:1306–1310, American Association for the Advancement of Science (1990).

Burgess, W.H. et al., "Possible Dissociation of the Heparin–binding and Mitogenic Activities of Heparin–binding (Acidic Fibroblast) Growth Factor–1 from its Receptor–binding Activities by Site–directed Mutagenesis of a Single Lysine Residue," *J. Cell Biol. 111*:2129–2138, The Rockefeller University Press (1990).

Burgess, W.H. et al., "Structure–Function Studies of FGF–1: Dissociation and Partial Reconstitution of Certain of Its Biological Activities," *Molec. Reprod. Devel. 39*:56–61, Wiley–Liss, Inc. (1994).

Cheng, H. et al., "Spinal Cord Repair in Adult Paraplegic Rats: Partial Restoration of Hind Limb Function," *Science 273*:510–513, American Association for the Advancement of Science (Jul. 1996).

Copeland, R.A. et al., "The Structure of Human Acidic Fibroblast Growth Factor and Its Interaction with Heparin, "*Arch. Biochem. Biophys. 289(1)*:53–61, Academic Press, Inc. (1991).

Cunningham, B.C. et al., "High–Resolution Epitope Mapping of hGH–Receptor Interactions by Alanine–Scanning Mutagenesis," *Science 244*:1081–1085, American Association for the Advancement of Science (1989).

Eriksson, A.E. et al., "Three–dimensional structure of human basic fibroblast growth factor," *Proc. Natl Acad. Sci USA 88*:3441–3445, National Academy of Sciences of the USA (1991).

Eriksson, A.E. et al., "Refinement of the structure of human basic fibroblast growth factor at 1.6 Å resolution and analysis of presumed heparin binding sites by selenate substitution," *Prot. Sci. 2*:1274–1284, Cambridge University Press (1993).

Faham, S. et al., "Heparin Structure and Interactions with Basic Fibroblast Growth Factor," *Science 271*:1116–1120, American Association for the Advancement of Science (Feb. 1996).

Fox, G.M. et al., "Production, Biological Activity, and Structure of Recombinant Basic Fibroblast Growth Factor and an Analog with Cysteine Replaced by Serine," *J. Biol. Chem. 263(34)*:18452–18458, The American Society for Biochemistry and Molecular Biology, Inc. (1988).

Friedman, S. et al., "Mutagenesis of the Nuclear Localization Sequence in FGF–1 Alters Protein Stability But Not Mitogenic Activity," *Biochem. Biophys. Res. Comm. 198(3)*:1203–1208, Academic Press, Inc. (1994).

Harper, J.W. and Lobb, R.R., "Reductive Methylation of Lysine Residues in Acidic Fibroblast Growth Factor: Effect on Mitogenic Activity and Heparin Affinity," *Biochemistry 27*:671–678, American Chemical Society (1998).

Heath, W.F. et al., "Mutations in the Heparin–Binding Domains of Human Basic Fibroblast Growth Factor Alter Its Biological Activity," *Biochemistry 30*:5608–5615, American Chemical Society (1991).

Henderson, B. and Blake, S., "Therapeutic potential of cytokine manipulation," *TIPS 13*:145–152, Elsevier Science Publishers Ltd (1992).

Imamura, T. et al., "Recovery of Mitogenic Activity of a Growth Factor Mutant with a Nuclear Translocation Sequence," *Science 249*:1567–1570, American Association for the Advancement of Science (1990).

Isacchi, A. et al., "A Mutant of Basic Fibroblast Growth Factor that Has Lost the Ability to Stimulate Plasminogen Activator Synthesis in Endothelial Cells," *Ann. Ny Acad. Sci. 638*:369–377, The New York Academy of Sciences (1991).

Isacchi, A. et al., "A six–amino acid deletion in basic fibroblast growth factor dissociates its mitogenic activity from its plasminogen activator–inducing capacity," *Proc. Natl. Acad. Sci. USA 88*:2628–2632, The National Academy of Sciences of the USA (1991).

Kusstatscher, S., et al., "Different Molecular Forms of Basic Fibroblast Growth Factor (bFGF) Accelerate Duodenal Ulcer Healing in Rats," *J. Pharmacol. Exp. Ther. 275*:456–461, Williams & Wilkins (1995).

Li, L.Y. et al., "Diminished Heparin Binding of a Basic Fibroblast Growth Factor Mutant Is Associated with Reduced Receptor Binding, Mitogenesis, Plasminogen Activator Induction, and *in Vitro* Angiogenesis," *Biochemistry 33*:10999–11007, American Chemical Society (1994).

Liszewski, K., "Companies Aim Novel Therapeutic Strategies at Dual Nature of Angiogenesis," *Gen Eng. News*, May 1, 1997 (6 pages), Mary Ann Liebert Inc. Publ.

Logan, A. and Berry, M., "Transforming growth factor–$\beta$ and basic fibroblast growth factor in the injured CNS," *TiPS 14*:337–343, Elsevier Science Publishers Ltd (1993).

Martin, P., "Wound Healing–Aiming for Perfect Skin Regeneration," *Science 276:* 75–81, American Association for the Advancement of Science (Apr. 1997).

Ornitz, D.M. et al., "FGF Binding and FGF Receptor Activated by Synthetic Heparan–Derived Di–and Trisaccharides," *Science 268*:432–436, American Association for the Advancement of Science (Apr. 1995).

Pantoliano, M.W. et al., "Multivalent Ligand–Receptor Binding Interactions in the Fibroblast Growth Factor System Produce a Cooperative Growth Factor and Heparin Mechanism for Receptor Dimerization," *Biochemistry 33*:10229–10248, American Chemical Society (1994).

Presta, M. et al., "Structural–Function Relationship of Basic Fibroblast Growth Factor: Site–Directed Mutagenesis of a Putative Heparin–Binding and Receptor–Binding Region," *Biochem. biophys. Res. Comm. 185(3)*:1098–1107, Academic Press, Inc. (1992).

Robinson, C.J., "Growth factors in wound healing," *TIBTECH 10*:301–302, Elsevier Science Publishers Ltd (1992).

Robson et al., "Modern Ideas and Notations Relating to Primary Structure," in *introduction to Proteins and Protein Engineering*, p.41, Elsevier, New York, New York (1986).

SCIOS Annual Report, "Fiblast: A Special Report," 8 pages, SCIOS (1996).

Seddon, A.P. et al., "Engineering of Fibroblast Growth Factor: Alteration of Receptor Binding Specificity," *Biochemistry 34*:731–736, American Chemical Society (1995).

Seno, M. et al., "Carboxyl–terminal structure of basic fibroblast growth factor significantly contributes to its affinity for heparin," *Eur. J. Biochem. 188*:239–245, Springer International (1990).

Slavin, J., "The Role of Cytokines in Wound Healing," *J. Pathol. 178*:5–10, John Wiley & Sons, Ltd. (Jan. 1996).

Springer, B.A. et al., "Identification and Concerted Function of Two Receptor Binding Surfaces on Basic Fibroblast Growth Factor Required for Mitogenesis," *J. Biol. Chem. 269(43)*:26879–26884, The American Society for Biochemistry and Molecular Biology, Inc. (1994).

Ten Dijke, P. and Iwata, K.K., "Growth Factors for Wound Healing," *Bio/Technology 7*:793–798, Nature Publishing Company (1989).

Thompson, L.D. et al., "Energetic Characterization of the Basic Fibroblast Growth Factor–Heparin Interaction: Identification of the Heparin Binding Domain," *Biochemistry 33(13):* 3831–3840, American Chemical Society (1994).

Van Brunt, J. and Klausner, A., "Growth Factors Speed Wound Healing," *Bio/Technology 6(1)*:25–30, Nature Publishing Company (1988).

Watson, J. et al., in *Molecular Biology of the Gene*, vol. I, Fourth Edition, 226–227, The Benjamin/Cummings Publishing Company, Inc., Menlo Park, California (1987).

Wong, P. et al , "Analysis of Putative Heparin–binding Domains of Fibroblast Growth Factor–1," *J. Biol. Chem. 270(43)*:25805–25811, The American Society for Biochemistry and Molecular Biology, Inc. (1995).

Young, W., "Spinal Cord Regeneration," *Science 273*:451, American Association for the Advancement of Science (Jul. 1996).

Zhang, J. et al., "The Three–dimensional structure of human basic fibroblast growth factor, a structural homolog of interleukin 1β," *Proc. Natl. Acad. Sci. USA 88*:3446–3450, National Academy of Science of the USA (1991).

Zhu, X. et al., "Structural studies of the binding of the anti–ulcer drug sucrose octasulfate to acidic fibroblast growth factor," *Structure 1*:27–34, Current Biology Ltd (1993).

Zhu, X., "Three–Dimensional Structures of Acidic and Basic Fibroblast Growth Factors," *Science 251*:90–93, American Association for the Advancement of Science (1991).

Zhu, H. et al., "Glu–96 of Basic Fibroblast Growth Factor is Essential for High Affinity Receptor Binding," *J. Biol. Chem. 270(37)*:21869–21874, The American Society for Biochemistry and Molecular Biology, Inc. (1995).

Patent Cooperation Treaty, International Search Report for PCT/US99/30534, mailed Sep. 1, 2000.

* cited by examiner

```
       1    NcoI
ATG GGC ACC ATG GCA GCC GGG AGC ATC ACC ACG CTG CCC GCC CTT CCG GAG
Met Gly Thr Met Ala Ala Gly Ser Ile Thr Thr Leu Pro Ala Leu Pro Glu

SmaI
GAT GGC GGC AGC GGC GCC TTC CCG CCC GGG CAC TTC AAG GAC CCC AAG CGG
Asp Gly Gly Ser Gly Ala Phe Pro Pro Gly His Phe Lys Asp Pro Lys Arg

CTG TAC TGC AAA AAC GGG GGC TTC TTC CTG CGC ATC CAC CCC GAC GGC CGA
Leu Tyr Cys Lys Asn Gly Gly Phe Phe Leu Arg Ile His Pro Asp Gly Arg

GTT GAC GGG GTC CGG GAG AAC AGC GAC CCT CAC ATC AAG CTA CAA CTT CAA
Val Asp Gly Val Arg Glu Lys Ser Asp Pro His Ile Lys Leu Gln Leu Gln

KpnI
GCA GAA GAG AGA GGA GTT GTG TCT ATC AAA GGA GTG TGT GCT AAC CGG TAC
Ala Glu Glu Arg Gly Val Val Ser Ile Lys Gly Val Cys Ala Asn Arg Tyr 89                                            101
CTG GCT ATG AAA|GAA|GAT GGT CGA CTG CTG GCT TCT AAA TGC GTT ACC|GAT|
Leu Ala Met Lys|Glu|Asp Gly Arg Leu Leu Ala Ser Lys Cys Val Thr|Asp|

XhoI
GAG TGC TTC TTC TTC GAA CGT CTC GAG TCT AAC AAC TAC AAC ACC TAC CGT
Glu Cys Phe Phe Phe Glu Arg Leu Glu Ser Asn Asn Tyr Asn Thr Tyr Arg

AflII
TCG AGA AAA TAC ACC AGT TGG TAT GTG GCA CTT AAG CGT ACC GGT CAG TAC
Ser Arg Lys Tyr Thr Ser Trp Tyr Val Ala Leu Lys Arg Thr Gly Gln Tyr

137             ApoI
AAA|CTT|GGT TCT AAG ACG GGC CCA GGT CAG AAA GCT ATC CTG TTC CTG CCG
Lys|Leu|Gly Ser Lys Thr Gly Pro Gly Gln Lys Ala Ile Leu Phe Leu Pro

BamHI
ATG TCT GCT AAA TCT TGA GGA TCC
Met Ser Ala Lys Ser ***
```

ANALOGS OF HUMAN BASIC FIBROBLAST GROWTH FACTOR MUTATED AT ONE OR MORE OF THE POSITIONS GLUTAMATE 89, ASPARTATE 101 OR LEUCINE 137

This is a continuation of U.S. patent application Ser. No. 09/220,077, filed Dec. 23, 1998, now U.S. Pat. No. 6,274,712)B1, which claims the benefit, under 35U.S.C. § 119(e), of the earlier filing date of U.S. provisional application. Appl. No. 60/068,667, filed on Dec. 23, 1997. The entirety of each of these applications is incorporated by reference herein.

BACKGROUND OF THE INVENTION

Statement as to Rights to Inventions Made Under Federally-sponsored Research and Development Part of the work performed during development of this invention utilized U.S. Government funds. The U.S. Government has certain rights in this invention.

1. Field of the Invention

The present invention relates to the identification of new muteins of human basic fibroblast growth factor that are unusually potent stimulators of cell division.

2. Description of the Related Art

Fibroblast growth factors (FGFs) are an evolutionarily conserved, large family of mitogenic proteins that stimulate mitosis in mesodermal and neuroectodermal cell lineages (Basilico, C. and Moscatelli, D., *Advances in Cancer Research* 59:115–165, Eds. Vande Woudc, G. F. and Klein, G. (1992)). These proteins also bind heparin and are often referred to in the literature as heparin binding growth factors (HBGFs). Family members share a high degree of nucleic acid and amino acid sequence homology.

Complementary DNA clones encoding basic FGF (bFGF), one member of the FGF family, have been isolated and sequenced. The protein is found to have 89 to 95% amino acid identity among several species, including human, bovine, and rat (Xenopus bFGF is more divergent, sharing 80% homology with human bFGF). This degree of conservation suggests that all regions of the protein may be functionally important. In humans, bFGF is expressed in four forms: (1) an 18-kDa form (155 amino acids) initiated from an AUG codon; (2), (3) and (4) that are 22, 22.5 and 24 kDA, respectively, and all initiated from the CUG codons resulting in N-terminal extensions of varying lengths relative to the 18 kDa font (Florkiewicz, R. Z. and Sommer, A., *Proc. Natl. Acad. Sci.* (USA) 86:3978–3981 (1989); Pratts, H., et al., *Proc. Natl. Acad. Sci.* (USA) 86:1836–1840 (1988)). Additionally, while the different forms of bFGF are localized in different compartments of the cell, there is only limited information relating to the functional significance of such subcellular localization. The biological activity of bFGF on cells in trans is effected through signal transduction after cell surface binding to an FGF specific receptor and to heparin sulfate proteoglycans (Moscatelli, D., *J. Cell Physiology.* 131:123–130 (1987)). In all tissues so far examined, bFGF is found to be expressed, perhaps reflecting its broad spectrum mitogenic activity.

Due to its ability to stimulate the proliferation of a wide variety of cell types, bFGF plays asignificant role in many biological processes: (1) angiogenesis (Folkrnan, J. and Klagsbrum, M., *Science* 235:442–447 (1987); (2) wound healing (Slavin, J., *J. Pathology* 178: 5–10, 1996; McGee, G. S., et al., *J. Surg. Research* 45:145–153 (1988); (3) embryogenesis (Kimelman, D., et al., *Science* 242:1050–1056 (1988): Herbert, J. M., et al., *Dev. Biol.* 138:454–463 (1990); and (4) tumorigenesis (Ulrich, R., et al., *Cancer Cell* 3(8):308–311 (1991); Nguyen, M., et al.,*J. Natl Cancer. Inst.* 86(5):356–361 (1994); Wright, J. A., et al., *Crit. Rev. Oncogenecsis* 4(5):473–492 (1993)). Also there is evidence indicating that bFGF may be used therapeutically in the treatment of cerebral ischemia (Lyons, M. K., et al.,*Brain Research* 558:315–320 (1991); Koketsu, N., et al., *Annals Neurology* 35(4):451–457 (1994), cerebral aneurysyms (Futami, K., et al., *Stroke* 26(9):1649–1654 (1995) and neural injury (Logan, A. and Berry, M., *TIPS* 14:337–343 (1993); Eckenstein, F. P., *J. Neurobiology* 25(11):1467–1480 (1994); Gomez-Pinilla, F., et al.,*J. Neuroscience* 15(3):2021–2029 (1995)), in addition to its therapeutic potential in the treatment of vascular disease (Richard, J-L., et al., *Diabetes Care* 18(1):64–69 (1995); Lindner, V., et al., *J. Clin. Invest.* 85:2004–2008 (1990); Lazarous, D. F., et al., *Circulation* 91(1):145–153 (1995)) and gastric and duodenal ulcers (Folkman, J., et al., *Ann. Surg.* 214(4):414–427 (1991): Szabo, S., et al., *Scand. J. Gastroenterology* 30 *Suppl*. 208:3–8 (1995); Kitijima, M., et al., *Microvasc. Research* 50:133–138(1995); Kusstatscher, S., et al.,*J. Pharm. Exp. Therapeutics* 275:456–461 (1995); Szabo, S., et al., *Gastroenterology* 106:1106–1111 (1994); Konturek, S. J., et al., Gut 34:881–887 (1993)).

In order to more fully understand this widespread, biologically significant ligand-receptor system, basic research in this field is focused on elucidating the relationship between bFGF protein structure and function. Early structural studies utilized synthetic peptides corresponding to different regions of the bFGF protein to grossly map the heparin binding and receptor binding regions of the protein (Baird et al., *Proc. Natl. Acad. Sci.* (USA) 85:2324–2328 (1988); Baird et al.,*J. Cell Phys. Suppl.* 5:101–106 (1987)). More recently, high resolution X-ray crystallography studies (Zhu et al., *Science* 252:90–93 (1991); Zhang et al., *Proc. Natl. Acad. Sci.* (USA) 88:3446–3450 (1991); Eriksson et al., *Proc. Natl. Acad. Sci.* (USA) 88:3441–3445 (1991)) have been used in structure-based, site-directed mutagenesis analyses (Thompson et al., *Biochemistry* 33(13):3831–3840 (1994); Springer et al., *J. Bio. Chem.* 269(43):26879–2688 (1994)) and biophysical characterizations of the interactions of bFGF with the bFGF receptor and heparin (Pantoliano et al., *Biochemistry* 33:10229–10248 (1994)) to further define the functional domains of the protein.

The studies of Thompson et al., Springer et al., and Pantoliano et al., have established the following: (1) the primary receptor binding domain (site 1) is a discontinuous domain, important points of contact being amino acids Y24, R44, N101, Y103, L140 and M142, which are exposed to solvent; (2) a secondary receptor binding domain (site 2) (approximately 250 fold weaker binding) is important for bFGF mitogenicity and comprises amino acids 106–115, which form a type-1 β-turn; and (3) the heparin binding domain which is also a discontinuous domain, the key amino acids of which are K26, N27, R81, K119, R120, T121, Q123, K125, K129, Q134 and K135. (Note: letter/number designations correspond to the single letter amino acid code followed by the position in the linear amino acid sequence for bFGF as described by Zhang et al., 1991. )

One current model of bFGF action suggests that the monomeric ligand bFGF binds to its cell surface receptor through both the high affinity domain (site 1) and the low affinity domain (site 2), leading to receptor dimerization and signal transduction. Heparin binding, known to be important for bFGF activity, is believed to promote site 2 binding to the receptor. (Pantoliano et al., *Biochemistry* 33:10229–10248 (1994)).

The amino acid sequence of wild-type bFGF is disclosed in several publications: for example, U.S. Pat. Nos. 5,155, 214; 4,994,559; 5,439,818; 5,604,293; European Patent Publication No. EP 0 237 966 A2, to name a few.

Structure/function information is useful in studying the biological activity of variants of the bFGF protein sequence. Consequently, there is a great deal of interest in generating new muteins of bFGF for study. For example, analogs in which at least one amino acid is substituted, preferably targeting Cys, Asp, Arg, Gly and Val residues, have been reported (International Publication No. WO 91/09126). Another publication describes a replacement mutein in which at least one cysteine residue is substituted with another amino acid, and deletion mutations in which either 41 amino acids are missing from the amino terminus or 61 amino acids are missing from the carboxyl terminus (U.S. Pat. No. 5,478,740). Mutations in the heparin binding domain of human bFGF are known to alter its biological activity (Heath et al., *Biochemistry* 30(22):5608–5615 (1991)) and the highly conserved Arg 40 and Arg 45 residues are necessary for stability and mitogenicity of bFGF (Arakawa et al., *J. Protein Chemistry* 14(5):263–274 (1995)). Additionally, enhanced stability analogs have been reported in which 2 or 3 amino acids are added, deleted or substituted, with serine substitution being preferred for cysteine residues (Eur. Pat. Pub. No. EP 0 281, 822 B2).

As previously disclosed, bFGF is a powerful mitogen and a key regulatory factor in many biological processes: for example angiogenesis, wound healing, ischemic tissue repair, gastric and duodenal ulcer healing, tumorigenesis and neural tissue survival and regeneration. Not surprisingly, the therapeutic value of wild-type and mutein bFGF's is recognized and detailed in the art, some examples of which are listed herein. Therapeutic treatments related to the above disclosed biological processes have been described for wild-type bFGF in U.S. Pat. Nos. 5,612,211; 5,439,818; 5,604, 293; 5,514,566; 4,994,559; 5,514,662 and European Patent Application No. EP 0 237 966 A2. Similar therapeutic treatments utilizing bFGF muteins are disclosed in U.S. Pat. Nos. 5,132,408; 5,352,589; 5,360,896; 5,371,206; 5,302, 702; 5,310,883; 5,478,804; 5,576,288 and European Patent Application No. EP 0 281 822 A2. For example, replacement muteins in which the loop region of human bFGF (amino acid residues 118–122) are replaced with selected peptides of other FGF family members are described in U.S. Pat. No. 5,491,220. These muteins are disclosed to be useful in the treatment of cancer as antiproliferative agents or as agents that promote vascularization.

Given the potential therapeutic value of the bFGF protein, there is a need in the art for the development of novel analogs of bFGF with improved biological properties.

SUMMARY OF THE INVENTION

It is therefore an object of the present invention to provide analogs of human bFGF with superagonist activity. Other objects, features and advantages of the present invention will be set forth in the detailed description of the preferred embodiments that follows, and in part, will be apparent from the description or may be learned by practice of the invention.

In a first embodiment, the present invention is directed to muteins of human bFGF in which Glutamate 89 or Aspartate 101 or Leucine 137 or combinations or permutations thereof are substituted with a neutral and/or hydrophobic amino acid. Other embodiments are drawn to polynucleotides encoding the muteins of the first embodiment, a vector containing said polynucleotide and a host cell carrying said vector. A third group of embodiments are drawn to processes to produce a polypeptide, to produce cells capable of producing said peptide and to produce a vector containing DNA or RNA encoding said polypeptide. A fourth group of embodiments are drawn to methods to stimulate cell division, to heal a wound, to treat ischemia, to treat peripheral vascular disease, to treat a gastric or duodenal ulcer, to treat neural injury and a pharmacologic composition comprising an effective amount of the mutein of the first embodiment.

It is to be understood that both the foregoing general description and the following detailed description are exemplary and explanatory only and are intended to provide further explanation of the invention as claimed.

BRIEF DESCRIPTION OF THE FIGURES

For reference purposes, the glycine at position 1 of this sequence corresponds to the first amino acid in the sequence reported by Sommer et al., *Biochem. Biophys. Res. Commun.* 144(2):543–550 (1997)), the methionine at amino acid position 3 of this sequence corresponds to the first amino acid reported for the 18 kDA form of human bFGF reported by Prats et al., *Proc. Natl. Acad. Sci.* (USA) 86(6) :1836–1840 (1989); GenBank Accession No. J04513) and the proline at position 12 of this sequence corresponds to the first amino acid in the human bFGF sequence reported in FIG. 4 of U.S. Pat. No. 5,439,818 by Fiddes et al.

The concentration of wild-type and mutant bFGF required to give the ½ maximal response ($ED_{50}$) was plotted and calculated using the following equation: $y=(m*x/(x+c))$, where y=absorbance, x=concentration of growth factor, m=the maximum response and $c=ED_{50}$. During each assay on mutant proteins, a parallel analysis was performed for wild-type bFGF. Our recombinant human wild-type bFGF expressed and purified from *E. coli* has been repeatedly shown to have an $ED_{50}$ value identical to the bFGF international standard (code 90/712) obtained from the National Institute for Biological Standards and Control.

Numbering of amino acids is based on the expression of a 157 amino acid form of bFGF as described in the Examples section and in FIG. 1. Amino acids are identified using the single letter code. Mutations are designated by the one letter code for the original amino acid, followed by the amino acid number, followed by the one letter code for the replacement amino acid.

The dose response data presented in FIG. 2 demonstrates that the $ED_{50}$ values for the bFGF muteins are significantly lower than that of wild-type bFGF.

DETAILED DESCRIPTION OF THE PREFERRED EMBODIMENTS

In a first embodiment, the present invention is drawn to a mutein of human basic fibroblast growth factor (bFGF), or biologically active peptide thereof, in which a neutral and/or hydrophobic amino acid has been substituted for one or more of the following amino acids: Glutamate 89, Aspartate 101 or Leucine 137.

A human bFGF mutein is defined as comprising human basic fibroblast growth factor in which at least one amino acid of the native protein has been substituted by another. Generally speaking, a mutein possesses some modified property, structural or functional, of the native protein. For example, the mutein may be antagonistic or agonistic with respect to normal properties of the native protein. An antagonist is defined as a substance that to some extent nullifies the action of another. For example, a molecule that binds a cell receptor without eliciting a biological response. An agonist is defined as a substance that induces a cellular or physiologic response. For example, a molecule that binds to a receptor and elicits a biological response. A biological response may be, for example, the stimulation of cell division, chemotaxis, angiogenesis or wound repair. A biological response may encompass other functional properties of the native protein and would be well known to those practicing the art. As used herein, these terms are not limiting, it being entirely possible that a given mutein is antagonistic to one biological response and agonistic with respect to another.

More specifically, the first preferred embodiment of the invention is human bFGF protein in which substitution means that any neutral and/or hydrophobic amino acid replaces at least one of the following: Glutamate 89, Aspartate 101 or Leucine 137. For clarity, the human bFGF protein sequence is presented in FIG. 1 to indicate exactly which amino acid residues are mutated. A neutral amino acid is defined to include serine, threonine, alanine, asparagine, glutamine, cysteine, glycine and non-naturally occurring analogues thereof. A hydrophobic amino acid is defined to include tyrosine, leucine, isoleucine, valine, proline, phenylalanine, tryptophan, methionine and non-naturally occurring analogues thereof.

Because one, two or three bFGF residues are possibly mutated in the bFGF mutein of the invention, the following numerical permutations are possible for mutein protein structure, where X stands for any neutral or hydrophobic amino acid, or non-naturally occurring analogue thereof: human bFGF [$X^{89}$], human bFGF [$X^{101}$], human bFGF [$X^{137}$], human bFGF [$X^{89}, X^{101}$], human bFGF [$X^{89}, X^{137}$], human bFGF [$X^{101}, X^{137}$] and human bFGF [$X^{89}, X^{101}, X^{137}$].

Therefore, in the first embodiment of the invention, X is defined as any neutral or hydrophobic amino acid. Consequently, where a mutein contains more than one of the described amino acid residue mutations, the substituted amino acid at a given particular mutated site may be a neutral or hydrophobic amino acid. For example, in one claimed embodiment of the invention, a neutral amino acid is defined as alanine, and a hydrophobic amino acid is defined as tyrosine. Thus, it will be obvious to one skilled in the art, referring to the above described numerical permutations for the bFGF mutein structure, that the number of possible amino acid sequence permutations depends on how X is defined: for example, human bFGF [$Ala^{89}, Tyr^{101}$], [$Tyr^{89}, Ala^{101}$] and others are indicated when X, a neutral or hydrophobic amino acid, is defined as alanine or tyrosine. In a more specific form of the first embodiment, the mutein of human basic FGF comprises the substitution of alanine for at least one of the following: Glutamate 89, Aspartate 101 or Leucine 137. The following muteins are indicated in the specific embodiment for alanine substitution identified above: human bFGF [$Ala^{89}$], human bFGF [$Ala^{101}$], human bFGF [$Ala^{137}$], human bFGF [$Ala^{89, 101}$], human bFGF [$Ala^{89, 137}$], human bFGF [$Ala^{101, 137}$] and human bFGF [$Ala^{89, 101, 137}$].

In another more specific form of the first embodiment, the mutein of human basic FGF comprises the substitution of tyrosine for at least one of the following: Glutamate 89, Aspartate 101 or Leucine 137. The following muteins are indicated in the specific embodiment for tyrosine substitution identified above: human bFGF [$Tyr^{89}$], human bFGF [$Tyr^{101}$], human bFGF [$Tyr^{137}$], human bFGF [$Tyr^{89, 101}$], human bFGF [$Tyr^{89, 137}$], human bFGF [$Tyr^{101, 137}$] and human bFGF [$Tyr^{89, 101, 137}$].

The mutein may be produced by any method known to those skilled in the art. These methods would include, but are not limited to, laboratory means such as encompassed by recombinant DNA technologies or through the chemical synthesis of human bFGF possessing a neutral or hydrophobic amino acid at one or more of the designated positions (Glutamate 89, Aspartate 101 or Leucine 137).

The mutein of the present invention is also seen to include any and all mutations known to those in the art so long as at least one of the residues identified in the invention is appropriately mutated. Examples of mutations in the art include the following: deletion mutein bFGF 1–146, bFGF [$Ala^{69}$, $Ser^{87}$], bFGF [$Arg^{19}$], bFGF [$Glu^{107}$], bFGF [$Glu^{123}$], bFGF [$Ile^{107}$], bFGF [$Glu^{107,123}$] and bFGF [$Arg^{19}$, $Lys^{123, 137}$] in Heath, W. F., et al., *Biochemistry* 30:5608–5615 (1991)); bFGF [$Ser^{69,87}$] in PCT Pub. WO 91/09126; bFGF [$Gln^{128}$], bFGF [$Gln^{138}$], bFGF [$Gln^{128,138}$], bFGF [$Gln^{129}$], bFGF [$Gln^{134}$], bFGF [$Gln^{129, 134}$] in Lu-Yuan, L., et al., *Biochemistry* 33:10999–11007 (1994)); bFGF loop replacement muteins (residues 118–122) in Seddon, A. P., et al. *Biochemistry* 34:731–736 (1995)); bFGF [$Ala^{96}$], bFGF [$Ala^{107}$], bFGF [Ala or Phe at 109–114] in Zhu, H., et al., *J. Biol. Chem.* 270(37):21869–21874 (1995)). These mutations possess a certain mitogenic potential or receptor or heparin-binding activity that may or may not provide a basis for antagonistic or agonistic activity, which in combination with the mutations of this invention, will provide for a bFGF molecule with unique properties. Additional muteins with specific mutations are known and others will be developed. The mutein of this invention may incorporate one or more of the mutations that are commonly known in the art at the time.

The most preferred method for producing the mutein is through recombinant DNA methodologies and is well known to those skilled in the art. Such methods are conveniently found in published laboratory methods manuals such as *Current Protocols in Molecular Biology* (John Wiley & Sons, Inc.), which is incorporated herein by reference. For example, any previously isolated clone encoding human basic FGF, or variants thereof, will serve as a starting point to introduce one or more of the designated substitutions utilizing the method of site-directed mutagenesis. The term "variants of bFGF" refers to all muteins disclosed in the prior art, as discussed above.

Additionally, the first preferred embodiment includes a biologically active peptide derived from the mutein described herein. Such a peptide will contain at least one of the substitutions described for the mutein and will possess biological activity. The peptide may be produced by any and all means known to those skilled in the art, examples of which include but are not limited to enzymatic digestion, chemical synthesis or recombinant DNA methodologies.

It is well established in the art that fragments or peptides of the bFGF protein are biologically active. For example, see the heparin-binding and receptor-binding experiments done by Baird et al., *Proc. Natl. Acad. Sci.* (USA) 85:2324–2328 (1988), and *J. Cell. Phys. Suppl.* 5:101–106(1987)). Furthermore, there is sufficient information relating protein structure to biological function for the bFGF protein that one of ordinary skill in the art knows how to select such peptides. For example, see bFGF schematic relating protein structure and function in Basilico, C. and Moscatelli, D., *Advances in Cancer Research* 59:115–165, Eds. Vande Woude, G. F. and Klein, G. (1992)).

Therefore, the selection of fragments or peptides of the mutein is based on criteria known in the art. The first criterion is based on the structural requirements for at least one of the mutations identified in the invention and a sufficient amount of additional residues for a reasonable expectation of biological function using structure/function information in the literature. The second criterion is based on a functional test to evaluate biological activity similar to what is already known in the art, e.g., a mitogenic assay or heparin-binding assay, such as the cell proliferation assay disclosed in Springer, B. A. et al., *J. Bio. Chem.* 269(43): 26879–26884 (1994)) and the heparin affinity chromatography disclosed in Thompson, L. D., et al., *Biochemistry* 33(13):3831–3840 (1993)).

The present invention also encompasses a polynucleotide encoding the above described mutein that may be in the form of RNA or in the form of DNA, which DNA includes cDNA, genomic DNA, and synthetic DNA. The DNA may be double-stranded or single-stranded. The coding sequence that encodes the mutein of the present invention may vary as a result of the redundancy or degeneracy of the genetic code.

Figure 1:
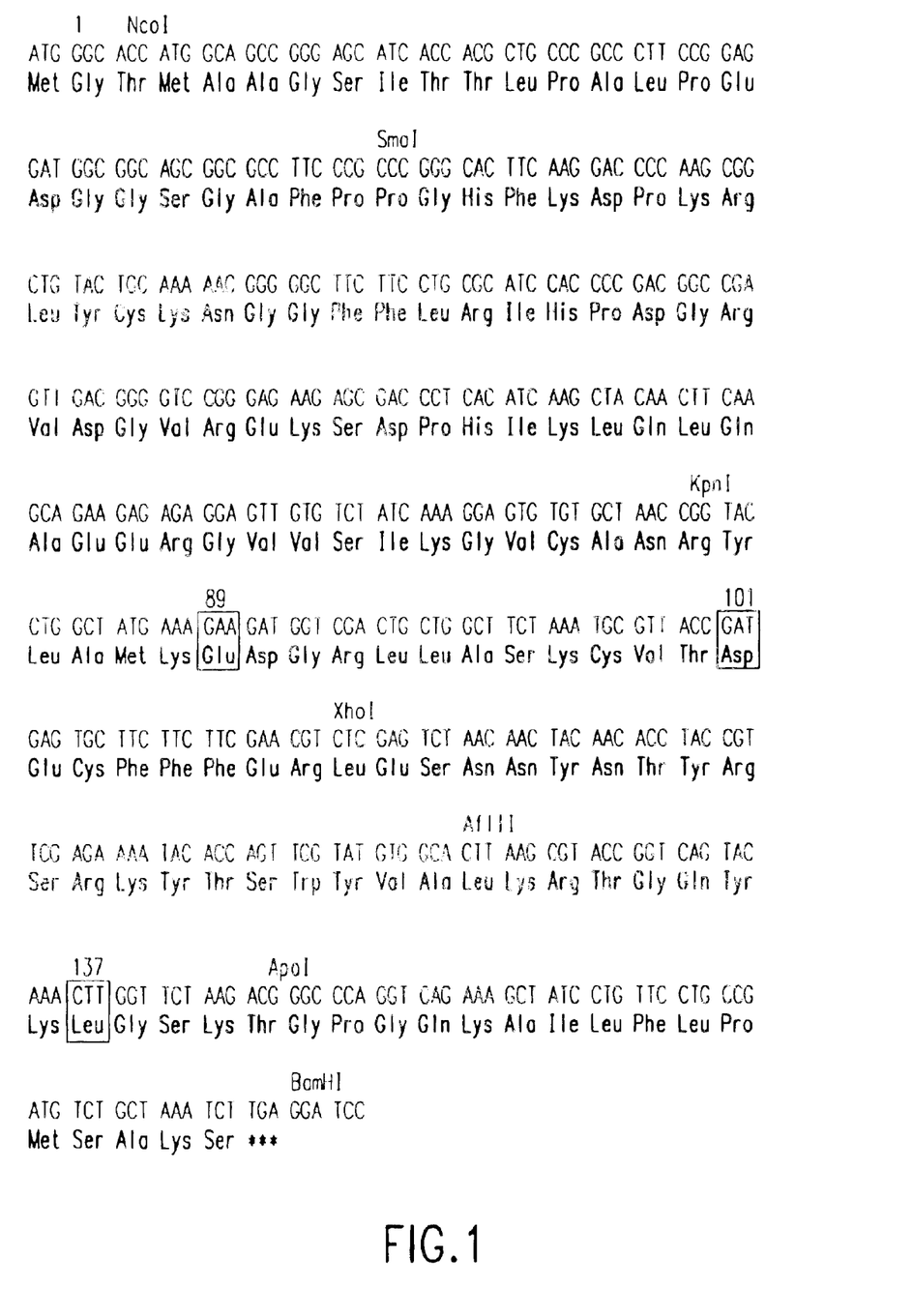
FIG. 1. This figure presents the DNA(SEQ ID NO:1) and amino acid (SEQ ID NO:2) sequence of the 157 amino acid form of bFGF used in this invention. The N-terminal, initiating methionine is processed by *E. coli*, and the purified bFGFs, therefore, lack the first amino acid shown in the figure. The nucleic acid sequence reported in this figure is representative of the wild-type bFGF DNA sequence following modifications of the gene purchased from R&D Systems. The DNA modifications were performed to incorporate restriction sites for subcloning and cassette mutagenesis; in all cases, the original amino acid sequence remained unaltered. The boxed and numbered amino acids identify those subjected to site-directed mutagenesis.

The polynucleotide that encodes for the mutein indicated in FIG. 1 may include the following: only the coding sequence for the mutein; the coding sequence for the mutein and additional coding sequence such as a functional polypeptide, or a leader or secretory sequence or a proprotein sequence; the coding sequence for the mutein (and optionally additional coding sequence) and non-coding sequence, such as introns or non-coding sequence 5' and/or 3' of the coding sequence for the mutein. Thus, the term "polynucleotide encoding a mutein" encompasses a polynucleotide which includes only coding sequence for the mutein as well as a polynucleotide which includes additional coding and/or non-coding sequence.

The present invention further relates to variants of the described polynucleotide that encode for fragments, analogs and derivatives of the polypeptide that contain the indicated substitutions. The variant of the polynucleotide may be a naturally occurring allelic variant of the human bFGF sequence or a non-naturally occurring variant. Thus, the present invention also includes polynucleotides encoding the mutein described above as well as variants of such polynucleotides which variants encode for a fragment, derivative or analog of the disclosed mutein. Such nucleotide variants include deletion variants, substitution variants and addition or insertion variants as long as at least one of the indicated amino acid substitutions is present. These nucleotide variants are most readily identified in the prior art as encoding muteins of the bFGF protein (discussed above).

As indicated, the polynucleotide may have a coding sequence which is a naturally occurring allelic variant of the sequence shown in FIG. 1. As known in the art, an allelic variant is an alternate form of a polynucleotide sequence which may have a substitution, deletion or addition of one or more nucleotides, which does not substantially alter the function of the encoded polypeptide.

The present invention also includes polynucleotides wherein the coding sequence for the mutein may be fused in the same reading frame to a polynucleotide sequence that aids in expression and secretion of a polypeptide from a host cell. For example, a leader sequence that functions as a secretory sequence for controlling transport of a polypeptide from the host cell. The polypeptide having a leader sequence is a preprotein and may have the leader sequence cleaved by the host cell to form the mature form of the polypeptide. The polynucleotides may also encode for a proprotein which is the mature protein plus additional N-terminal amino acid residues. A mature protein having a prosequence is a proprotein and is an inactive form of the protein. Once the prosequence is cleaved an active mature protein remains. Thus, for example, the polynucleotide of the present invention may encode the mutein, or the mutein having a prosequence or the mutein-having both a prosequence and a presequence (leader sequence).

The polynucleotide of the mutein also may encode for a chimeric molecule that contains, in part or in whole, the mutein coding sequence and the coding sequence of any other gene, or part thereof, known in the art. The nonmutein coding sequence may be positioned either 3' or 5' of the mutein coding sequence. The resultant chimeric protein contains properties of both the mutein and nonmutein protein. Examples of such a chimeric protein include, but are not limited to, the coding sequence of another growth factor, a protein that stabilizes the FGF mutein or a protein that targets the peptide to a particular tissue or cell type.

The mutein of the present invention may also have the coding sequence fused in frame to a marker sequence which allows for purification of the mutein of the present invention. The marker sequence may be a hexa-histidine tag or the T7 peptide (amino acid sequence: Met Ala Ser Met Thr Gly Gly Gln Gln Met Gly (SEQ ID NO:4)) supplied by a vector to provide for purification of the polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson. I., et al., *Cell* 37:767 (1984)). Other marker sequences well known to those skilled in the art may be used for similar purposes.

The appropriate DNA sequence may be inserted into the vector by a variety of procedures. In general, the DNA sequence is inserted into an appropriate restriction endonuclease site by procedures known in the art.

The DNA sequence in the expression vector is operatively linked to an appropriate expression control sequence (promoter) to direct mRNA synthesis. As representative examples of such promoters, there may be mentioned: LTR or SV40 promoter, the *E. coli* lac or trp, the phage lambda $P_L$ promoter, the T7 phage promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence, as well as an appropriate promoter or control sequence, is employed to transform an appropriate host to permit the host to express the protein. As representative examples of appropriate hosts, there may be mentioned: bacterial cells, such as *E. coli, Salmonella tyiphimurium*, Streptomyces; fungal cells, such as yeast; insect cells, such as Drosophila and Sf9; animal cells such as CHO, COS or Bowes melanoma; plant cells, etc. The selection of an appropriate host is deemed to be within the scope of those skilled in the art.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art and are commercially available. The following vectors are provided by way of example: Bacterial- pET (Novagen), pQE70, pQE60, pQE-9 (Qiagen), pBs, phagescript, psiX174, pBlue-Script SK, pBsKS, pNH8a, pNH16a, pNH18a, pNH46a (Stratagene); pTrc99A, pKK223-3, pKK233-3, pDR540, pRIT5 (Pharmacia); and Eukaryotic- pWLneo, pSV2cat, pOG44, pXT1, pSG (Stratagene) pSVK3, pBPV, pMSG, pSVL (Pharmacia). Thus, these and any other plasmids or vectors may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include laci, lacz, T3, T7, gpt, lambda $P_R$, $P_L$ and trp. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation, techniques well known in the art.

The constructs in host cells can be used in a conventional manner to produce the gene product encoded by the recombinant sequence. Alternatively, the polypeptides of the invention can be synthetically produced by conventional peptide synthesizers.

The bFGF mutein can be expressed in mammalian cells, insect, yeast, bacterial, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., *Molecular Cloning: A Laboratory Manual*, Second Edition, Cold Spring Harbor, N.Y., 1989, the disclosure of which is hereby incorporated by reference.

Transcription of a DNA encoding the mutein of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and the *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence, to be expressed.

Following transformation of a suitable host strain and growth of the host strain to an appropriate cell density, the selected promoter is derepressed by appropriate means (e.g., temperature shift or chemical induction) and cells are cultured for an additional period. Cells are typically harvested by centrifugation, disrupted by physical or chemical means, and the resulting crude extract retained for further purification. Microbial cells employed for the expression of foreign proteins can be disrupted by any convenient method, including freeze-thaw cycling, sonication, mechanical disruption, or cell lysing agents.

Various mammalian cell culture systems can also be employed to express the mutein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

RNA vectors may also be utilized for the expression of the muteins disclosed in this invention. These vectors are based on positive or negative strand RNA viruses that naturally replicate in a wide variety of eukaryotic cells (Bredenbeek, P. J. and Rice, C. M., *Virology* 3:297–310 (1992)). Unlike retroviruses, these viruses lack an intermediate DNA lifecycle phase, existing entirely in RNA form. For example, alpha viruses are used as expression vectors for foreign proteins because they can be utilized in a broad range of host cells and provide a high level of expression; examples of viruses of this type include the Sindbis virus and Semliki Forest virus (Schlesinger, S., *TIBTECH* 11:18–22 (1993); Frolov, I., et al., *Proc. Natl. Acad. Sci.* (USA) 93:11371–11377 (1996)). As exemplified by Invitrogen's Sinbis expression system, the investigator may conveniently maintain the recombinant molecule in DNA form (pSinrep5 plasmid) in the laboratory, but propagation in RNA form is feasible as well. In the host cell used for expression, the vector containing the gene of interest exists completely in RNA form and may be continuously propagated in that state if desired.

The mutein is recovered and purified from recombinant cell cultures by methods established in the art, which include but are not limited to ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. Protein refolding steps can be used, as necessary, in completing configuration of the mature protein. Finally, high performance liquid chromatography (HPLC) can be employed for final purification steps.

Another embodiment of the invention relates to a method of stimulating cell division by contacting cells with the bFGF muteins described herein. Typically, stimulating cell division means that cells enter into and complete mitosis. Practically, this means that the cell population number doubles and increases exponentially. Contacting cells with the mutein is accomplished by any means known to those skilled in the art. In one embodiment, contact may occur in vitro. This would be particularly useful if an isolated population of a patient's or donor's (human or nonhuman) cells required expansion of cell number. In this instance the cells may be cultivated in vitro, by means well known to those practicing the art, in a nutrient medium containing a sufficient quantity of one or more of the bFGF muteins. Preferably, the mutein would be present at 0.001 picograms to 1000 micrograms per milliliter, more preferably at 0.001 nanograms to 1000 nanograms per milliliter and most preferably at 0.01 nanograms to 100 nanograms per milliliter concentration.

In another embodiment, contact may occur in vivo. In this preferred therapeutic approach, an animal suffering from a wound, ischemia, heart disease (e.g., coronary artery disease), peripheral vascular disease, a gastric or duodenal ulcer, stroke or neural injury is treated by administering to the animal a composition comprising one or more of the isolated bFGF muteins of the invention. The composition may be a pharmaceutical composition comprising a therapeutically effective amount of one or more isolated bFGF muteins of the invention and optionally a pharmaceutically acceptable carrier or excipient therefor. The administration of a bFGF composition promotes healing in conditions such as a wound, ischemia, heart disease (e.g., coronary artery disease), peripheral vascular disease, a gastric or duodenal ulcer, stroke or neural injury through the mitogenic, trophic, angiogenic, neuroprotective or other inherent property of the bFGF muteins described herein.

The bFGF mutein-containing compositions should be formulated and dosed in a fashion consistent with good medical practice, taking into account the clinical condition of the patient, the site of delivery of the bFGF mutein composition, the method of administration, the scheduling of administration, and other factors known to practitioners. The "therapeutically effective amount" of the bFGF mutein for purposes herein is thus determined by such considerations.

The bFGF muteins and the pharmaceutical compositions of the present invention may be administered by any means that achieve the generally intended purpose: to promote the healing of tissue damaged through trauma or disease. For example, administration may be by oral, ocular, otical, rectal, parenteral, subcutaneous, intravenous, intramuscular, intraperitoneal, intravaginal, topical (as by powders, ointments, drops or transdermal patch), bucal, intrathecal or intracranial routes, as an oral or nasal spray or as ocular or intraotic drops. The term "parenteral" as used herein refers to modes of administration which include intravenous, intramuscular, intraperitoneal, intrasternal, subcutaneous and intraarticular injection and infusion. The dosage administered will be dependent upon the age, health, and weight of the recipient, kind of concurrent treatment, if any, frequency of treatment, and the nature of the effect desired. Compositions within the scope of the invention include all compositions wherein a bFGF mutein is present in an amount that is effective to achieve the desired medical effect for treatment of a wound, ischemia, heart disease (e.g., coronary artery disease), peripheral vascular disease, a gastric or duodenal ulcer, stroke or neural injury. While individual needs may vary from one patient to another, the determination of the optimal ranges of effective amounts of all of the component is within the ability of the clinician of ordinary skill.

Generally, the formulations are prepared by contacting a bFGF mutein of the invention uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as are liposomes. Aqueous and non-aqueous vehicles would preferably be maintained at a pH of about 3 to 10. Also, it will be understood that the use of certain of the foregoing excipients, carriers, or stabilizers may result in the formation of bFGF mutein polypeptide salts.

For parenteral administration, in one embodiment, the bFGF muteins are formulated generally by mixing one or more of them at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

As a general proposition, the total therapeutically effective amount of bFGF mutein administered parenterally per dose will be from about 0.001 pg/kg body weight to about 10 mg/kg body weight daily and in most cases it would be administered in a dosage from about 1 pg/kg body weight to 5 mg/kg body weight per day and preferably the dosage is from about 10 pg/kg body weight to about 1 mg/kg body weight daily, taking into account the routes of administration, symptoms, etc. If given continuously, the bFGF mutein(s) may be administered either by 1–10 injections per day or by continuous subcutaneous infusion, for example, using a mini-pump. An intravenous bag solution may also be employed. The key factor in selecting an appropriate dose is the result obtained, as measured, for example, by increases in the circulating bFGF mutein level or by determining the extent to which healing is promoted. Other useful measures of determining therapeutic effectiveness are known to one of ordinary skill in the art. The length of treatment needed to observe changes, and the interval following treatment for responses to occur, may vary depending on the desired effect.

Pharmaceutical compositions for use in such methods comprise one or more of the isolated bFGF muteins of the present invention and may optionally comprise a pharmaceutically acceptable carrier or excipient therefor, as described above.

In another embodiment of the invention, a localized, topical application of one or more of the bFGF muteins would be a particularly preferred route of administration to promote the healing of a wound. Additionally, a localized application of one or more of the bFGF muteins may also be used in a treatment designed to promote the healing of damaged internal tissue or the growth of new tissue. For the purposes of this application, internal tissue may refer to bone, tendon, cartilage muscle, neural or other tissues and cells known by one skilled in the art to be responsive to basic Fibroblast Growth Factor. Damage may result from an extrinsic process such as an accident or surgery, or alternatively, damage may be the result of an intrinsic process, such as a disease, as what might be found in the case of heart disease (e.g., coronary artery disease; myocardial infarction), peripheral vascular disease, gastric and duodenal ulcers, stroke or neural disease processes as observed with Alzheimer's or Parkinson's Disease.

If a localized, external application is desired, then the bFGF muteins may be applied in pharmaceutical composition such as an ointment, gel, or other appropriately known carrier in according to guidelines established with the previously described pharmaceutical carriers. An internally localized application of a bFGF mutein composition may be obtained by direct application of it previously described pharmaceutical composition, or the bFGF mutein compositions may be administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773,919; EP 0 058 481), copolymers of L-glutamic acid and gamma-ethyl-L-glutamate (Sidman, U., et al., *Biopolymers* 22:547–556 (1983), poly (2-hydroxyethyl methacrylate) (Langer, R., et al., *J. Biomed. Mat. Res.* 15:167–277 (1981); Langer, R., *Chem. Tech.* 12:98–105 (1982), ethylene vinyl acetate (Langer et al., Id.) and poly-D(−)-3-hydroxybutyric acid (EP 0 133 988). Sustained-release bFGF mutein compositions may also include liposomally entrapped or absorbed bFGF muteins, which may be prepared by any of a variety of methods that have been well-described in the art (See U.S. Pat. Nos. 4,485,045 and 4,544,545; Epstein et al., *Proc. Natl. Acad. Sci.* (USA) 82:3688–3692 (1985); Hwang et al., *Proc. Natl. Acad Sci.* (USA) 77:4030–4034 (1980); EP 0 036 676; EP 0 052 322; EP 0 088 046; EP 0 102 324; EP 0 142 641; EP 0 143 949; DE 3,218,121; and JP 83-118008).

As a general rule, the therapeutic objective in a localized treatment protocol is to obtain a tissue concentration of the bFGF mutein that is ten times the normal bFGF tissue concentration (5 to 50 ng per gm wet weight tissue) and one hundred times the normal serum level of bFGF (Buckley, R., *Proc. Natl. Acad. Sci.* (USA) 82:7340–7344 (1985)). Thus, the aforementioned slow release polymers can be designed by those skilled in the art with this target concentration in mind. In the treatment of a wound, this would generally be accomplished through the application of a solution, ointment, gel, etc. containing 0.1 to 10 percent bFGF mutein. Effectively, this means the application of 0.1 to 100 micrograms of bFGF mutein(s) per square centimeter of wound area. It is anticipated that the exact dosage will vary depending on the circumstances; for example, the initial treatment for a third degree burn would be about 100 $\mu$g/cm$^2$ and, as the condition improved, the application of bFGF mutein would be decreased to about 0.1 $\mu$g/cm$^2$.

In another embodiment of the invention, the bFGF muteins may be combined in a pharmaceutical composition with another growth factor such as vascular endothelial cell growth factor, epidermal growth factor, platelet-derived growth factor, or any other cytokine known to one skilled in the art which would promote the healing of the aforementioned target tissues.

The bFGF muteins to be used for therapeutic administration must be sterile. Sterility is readily accomplished by filtration through sterile filtration membranes (e.g., 0.2 micron membranes) or by gamma or ultraviolet irradiation according to art-known techniques. Therapeutic bFGF mutein(s) polypeptide compositions generally are placed into a container having a sterile access port, for example, an intravenous solution bag or vial having a stopper pierceable by a hypodermic injection needle.

The therapeutic compositions comprising the bFGF muteins of the invention ordinarily may be stored in unit or multi-dose containers, for example, sealed ampules or vials, as an aqueous solution or as a lyophilized formulation for reconstitution. As an example of a lyophilized formulation. 10-ml vials are filled with 5 ml of sterile-filtered 1% (w/v) aqueous bFGF mutein solution, and the resulting mixture is lyophilized. The infusion solution is prepared by reconstituting the lyophilized bFGF mutein using U.S.P. water that is suitable for injection.

The invention also provides a pharmaceutical pack or kit comprising one or more containers filled with one or more of the ingredients of the pharmaceutical compositions of the invention. Associated with such containers can be a notice in the form prescribed by a governmental agency regulating the manufacture, use or sale of pharmaceuticals or biological products, which notice reflects approval by the agency of manufacture, use or sale for human administration. In addition, a mutein of the present invention may be employed in conjunction with other therapeutic compounds.

In another embodiment of the invention, an animal suffering from a wound, ischemia, heart disease (e.g., coronary, artery disease), peripheral vascular disease, gastric or duodenal ulcers, stroke or neural injury may be treated by introducing into the animal one or more of the isolated nucleic acid molecules of the invention comprising a polynucleotide encoding one or more of the bFGF muteins or a fragments thereof. This approach, known generically as "gene therapy", generally targets somatic cells as a means of treating inherited diseases, cancer and acquired disorders (Bank, A., Bioessays 18(12):999–1007 (1996)). This embodiment is designed to increase the level of bFGF mutein gene expression in and around the tissue and cells wherein the medical objective is to promote healing or new tissue growth.

Initial research in the area of gene therapy focused on a few well-characterized and highly publicized disorders: cystic fibrosis-Drumm, M. L. et al., Cell 62:1227–1233 (1990); Gregory, R. J. et al., Nature 347:358–363 (1990); Rich, D. P. et al., Nature 347:358–363 (1990); and Gaucher disease-Sorge, J. et al., Proc. Natl. Acad. Sci. (USA) 84:906–909 (1987); Fink, J. K. et al., Proc. Natl. Acad. Sci. (USA) 87:2334–2338 (1990); and certain forms of hemophilia-Bontempo, F. A. et al., Blood 69:1721–1724 (1987); Palmer, T. D. et al., Blood 73:438–445 (1989); Axelrod, J. H. et al., Proc. Natl. Acad. Sci. (USA) 87:5173–5177 (1990); Armentano, D. et al., Proc. Natl. Acad. Sci. (USA) 87:6141–6145 (1990); and muscular dystrophy- Partridge, T. A. et al., Nature 337:176–179 (1989); Law, P. K. et al., Lancet 336:114–115 (1990); Morgan, J. E. et al., J. Cell Biol. 111:2437–2449 (1990).

More recently, the application of gene therapy in the treatment of a wider variety of disorders is progressing, for example: cancer (Runnebaum, I. B., Anticancer Res. 17(4B) :2887–2890 (1997), heart disease (Rader, D. J., Int. J. Clin. Lab. Res. 27(1):35–43 (1997); Malosky, S., Curr. Opin. Cardiol. 11(4):361–368 (1996)), central nervous system disorders and injuries (Yang, K., et al., Neurotrauma J. 14(5):281–297 (1997); Zlokovic, B. V., et al., Neurosurgery 40(4):789–803 (1997); Zlokovic, B. V., et al., Neurosurgery 40(4):805–812 (1997), vascular diseases (Clowes. A. W., Thromb. Haemost. 78(1):605–610 (1997), muscle disorders (Douglas, J. T., et al., Neuromuscul. Disord. 7(5):284–298 (1997); Huard, J., et al., Neuromuscul. Disord. 7(5):299–313 (1997)), rheumatoid arthritis (Evans, C. H., et al., Curr. Opin. Rheumatol. 8(3): 230–234 (1996)) and epithelial tissue disorders (Greenhalgh, D. A., et al., Invest Dermatol. J. 103(5 Suppl.):63S–93S (1994)).

In a preferred approach, one or more isolated nucleic acid molecules of the invention is introduced into or administered to the animal. Such isolated nucleic acid molecules may be incorporated into a vector or virion suitable for introducing the nucleic acid molecules into the cells or tissues of the animal to be treated, to form a transfection vector. Techniques for the formation of vectors or virions comprising the bFGF mutein-encoding nucleic acid molecules are well-known in the art and are generally described in "Working Toward Human Gene Therapy," Chapter 28 in Recombinant DNA, 2nd Ed., Watson, J. D. et al., eds., New York: Scientific American Books, pp.567–581 (1992). An overview of suitable vectors or virions is provided in an article by Wilson, J. M., Clin. Exp. Immunol. 107(Suppl. 1):31–32 (1997)). Such vectors are derived from viruses that contain RNA (Vile, R. G., et al., Br. Med Bull. 51(1):12–30 (1995)) or DNA (Ali M., et al., Gene Ther. 1(6):367–384 (1994)). Example vector systems utilized in the art include the following: retroviruses (Vile, R. G., supra.), adenoviruses (Brody, S. L. et al., Ann. N. Y. Acad. Sci. 716:90–101 (1994)), adenoviral/retroviral chimeras (Bilbao, G., et al., FASEB J. 11(8):624–634 (1997), adeno-associated viruses (Flotte, T. R. and Carter, B. J., Gene Ther. 2(6):357–362 (1995)), herpes simplex virus (Latchman, D. S., Mol. Biotechnol. 2(2):179–195 (1994)), Parvovirus (Shaughnessy, E., et al., Semin Oncol. 23(1):159–171 (1996)) and reticuloendotheliosis virus (Donburg, R., Gene Therap. 2(5) :301–310 (1995)). Also of interest in the art, the development of extrachromosomal replicating vectors for gene therapy (Calos, M. P., Trends Genet. 12(11):463–466 (1996)).

Other, nonviral, methods for gene transfer known in the art (Abdallah, B., et al., Biol Cell 85(1):1–7 (1995)) might be utilized for the introduction of bFGF mutein polynucleotides into target cells; for example, receptor-mediated DNA delivery (Philips, S. C., Biologicals 23(1):13–16 (1995)) and lipidic vector systems (Lee, R. J. and Huang, L., Crit. Rev. Ther. Drug Carrier Syst. 14(2):173–206 (1997)) are promising alternatives to viral-based delivery systems.

General methods for construction of gene therapy vectors and the introduction thereof into affected animals for therapeutic purposes may he obtained in the above-referenced publications, the disclosures of which are specifically incorporated herein by reference in their entirety. In one such general method, vectors comprising the isolated polynucleotides of the present invention are directly introduced into target cells or tissues of the affected animal, preferably by injection, inhalation, ingestion or introduction into a mucous membrane via solution; such an approach is generally referred to as "in vivo" gene therapy. Alternatively, cells, tissues or organs, particularly those associated with a wound, ischemia, heart disease (e.g., coronary artery disease), peripheral vascular disease, a gastric or duodenal ulcer, stroke or neural injury, may be removed from the affected animal and placed into culture according to methods that are well-known to one of ordinary skill in the art; the vectors comprising the bFGF mutein polynucleotides may then be introduced into these cells or tissues by any of the methods described generally above for introducing isolated polynucleotides into a cell or tissue, and, after a sufficient amount of time to allow incorporation of the bFGF mutein polynucleotides, the cells or tissues may then be re-inserted into the affected animal. Since the introduction of the bFGF mutein gene is performed outside of the body of the affected animal, this approach is generally referred to as "ex vivo" gene therapy.

For both in vivo and ex vivo gene therapy, the isolated bFGF mutein polynucleotides of the invention may alternatively be operatively linked to a regulatory DNA sequence, which may be a bFGF mutein promoter or an enhancer, or a heterologous regulatory DNA sequence such as a promoter or enhancer derived from a different gene, cell or organism, to form a genetic construct as described above. This genetic construct may then be inserted into a vector, which is then used in a gene therapy protocol. The need for transcriptionally targeted and regulatable vectors providing cell-type specific and inducible promoters is well recognized in the art (Miller, N. and Whelan, J., Hum. Gene Therap. 8(7) :803–815 (1997); and Walther, W. and Stein, U., Mol. Med J. 74(7):379–392 (1996)), and for the purposes of bFGF mutein gene therapy, is incorporated herein by reference.

The construct/vector may be introduced into the animal by an in vivo gene therapy approach, e.g., by direct injection into the target tissue, or into the cells or tissues of the affected animal in an ex vivo approach. In another preferred embodiment, the genetic construct of the invention may be introduced into the cells or tissues of the animal, either in vivo or ex vivo, in a molecular conjugate with a virus (e.g., an adenovirus or an adeno-associated virus) or viral components (e.g., viral capsid proteins; see WO 93/07283). Alternatively, transfected host cells, which may be homologous or heterologous, may be encapsulated within a semipermeable barrier device and implanted into the affected animal, allowing passage of bFGF mutein polypeptides into the tissues and circulation of the animal but preventing contact between the animal's immune system and the transfected cells (see WO 93/09222). These approaches result in increased production of bFGF mutein by the treated animal via (a) random insertion of the bFGF mutein gene into the host cell genome; or (b) incorporation of the bFGF mutein gene into the nucleus of the cells where it may exist as an extrachromosomal genetic element. General descriptions of such methods and approaches to gene therapy may be found, for example, in U.S. Pat. No. 5,578,461; WO 94/12650; and WO 93/09222.

The methods of the invention are particularly well-suited for the medical treatment of a wound, ischemia, heart disease (e.g., coronary artery disease), peripheral vascular disease, gastric or duodenal ulcers, stroke or neural injury in any animal, preferably in mammals and most particularly in humans. It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

All patents and publications referred to herein are expressly incorporated by reference.

EXAMPLES

General Materials and Methods

Chemicals and Reagents: All restriction enzymes, T4 DNA ligase, T4 polynucleotide kinase and Litmus vectors were purchased from New England Biolabs (Beverly, Mass.). Oligonucleotide synthesis was provided by Gibco BRL (Gaithersburg, Md.); pET expression vectors and BL21 (DE3) competent cells were purchased from Novagen (Madison, Wis.), and the Sculptor™ in vitro mutagenesis system was purchased from Amersham (Arlington Heights, Ill.). DNA preparations were accomplished using Qiagen products and protocols (Chatsworth, Calif.). Protease inhibitors PMSF, leupeptin and pepstatin A were purchased from Sigma (St. Louis, Mo.), and DTT was purchased from Pierce (Rockford, Ill.). The CellTiter®96 Aq$_{uenus}$ Non-Radioactive Cell Proliferation Assay was purchased from Promega (Madison, Wis.). Cell culture reagents were purchased from Gibco (Grand Island, N.Y.).

Abbreviations: bFGF, basic fibroblast growth factor; DTT, Dithiothreitol; PMSF, phenylmethanesulfonyl fluoride; Hepes, -(2-hydroxyethyl)piperazine-N'-2-ethanesulfonic acid; EDTA, ethylenediamine tetra acetic acid; SDS-PAGE, sodium dodecyl sulfate polyacrylamide gel electrophoresis; IPTG, isopropyl p-D-thiogalactopyranoside; DMEM. Dulbecco's Modified Eagle's Media.

Example 1

Construction of bFGF Muteins

A synthetic gene for human basic fibroblast growth factor (bFGF) was purchased from R&D Systems (Minneapolis, Minn.) and is based on the published cDNA sequence (J. A. Abraham, *EMBO J*. 5(10) :2523–2328 (1986)). Numerous modifications of this gene were made by site-directed mutagenesis to incorporate unique restriction enzyme sites. In all cases the translated amino acid sequence was unaltered. The resultant DNA and amino acid sequence is found in FIG. 1.

Site-Directed Mutagenesis of the bFGF gene was accomplished by subcloning the bFGF sequence into the phagemid vector Litmus 28 (New England Biolabs, Beverly, Mass.). Single stranded DNA template was purified from phage following infection with helper phage. The initial mutations at amino acid positions E89 and D101 were made by single stranded DNA site-directed mutagenesis using the Sculptor™ in vitro mutagenesis system (Amersham, Arlington Heights, Ill.) according to the manufacturer's recommendations. The E89A, E89Y and D101A single site mutations were achieved using this method. Mutant DNA constructs were then subcloned back into the pET vector for expression of protein (see below).

All other mutations reported in Table 1 were constructed using cassette mutagenesis. The L137A mutation was made by inserting complementary oligonucleotides into the AflII and ApaI sites in which the CTT codon for leucine was replaced with the GCT codon for alanine (FIG. 1). A HindIII site (not shown) was removed for convenient screening of positives. The DNA sequence for the above mentioned mutations differs somewhat from that which appears in FIG. 1 although the amino acid sequence remains identical except for the introduced site-directed mutations. The DNA sequence for the E89A, E89Y, D101 A and L137A mutants differs from that reported in FIG. 1 only between the KpnI and ApaI restriction enzyme sites. Except for the introduced mutation (boxed codon in FIG. 1) the following DNA sequence between the KpnI and ApaI sites is representative for the E89A, E89Y, D101A and L137A mutants: CTGGC-TATGAAGGAAGATGGAAGATTACTGGCT-TCTAAATGTGTTA CGGATGAGTGTTTCTTTTTT-GAACGATTGGAATCTAATAACTACAAT ACTTAC-CGCTCGAGAAAATACACCAGTTGGTATGTGG-CACTTAAGC GTACCGGTCAGTACAAGCT-TGGTTCTAAAACGGGCC(SEQ ID NO:3). The E89A and D101A double mutation reported in Table 1 was constructed by inserting complementary oligonucleotides into the KpnI and XhoI sites (FIG. 1). The E89A, D101A, L137A triple mutant was constructed by combining the E89A. D101A double mutant with the single L137A mutant using the restriction enzyme sites engineered into the DNA sequence (FIG. 1). All mutations were confirmed by DNA sequencing of plasmid DNA. Cassette mutagenesis was performed using the bFGF expression construct (see below) such that no further subcloning was required.

Example 2

Expression and Purification of bFGF Muteins

Expression of wild-type and mutant proteins was performed using a modified pET expression vector as reported by Squires et al., *J. Biol. Chem*. 263: 16297–16302 (1989)) using the two-cistron method originally reported by Schoner et al., *Proc. Natl. Acad. Sci*. (USA) 83:8506–8510 (1986)). DNA was transformed into competent BL21(DE3) *Escherichia coli*, and single colonies were chosen for larger scale growth. Fermentations were either done on a 5 Liter scale with a BioFlo II fermenter from New Brunswick at the Bioprocessing Resource Center at Penn State University (University Park, Pa.) or in house using 2 Liter baffled shake flasks.

When fermented in the New Brunswick fermenter, 50 ml Luria Broth (10 gm tryptone, 5 gm yeast extract, 5 gm NaCl per liter) containing 50μg/ml carbenicillin was inoculated with the construct of choice transformed into BL21(DE3) and grown overnight. The 50 ml overnight culture was then used to inoculate a 5 liter volume of Super Broth (35 gm tryptone, 20 gm yeast extract. 5 gm NaCl per liter) containing 50 μg/ml of carbenicillin. Growth was continued until the $OD_{600mm}$ reached between 8–10 at which time IPTG (isopropyl β-D-thiogalactopyranoside) was added to a final concentration of 10 mM to induce expression of the T7 polymerase gene from BL21(DE3) cells. Cells were harvested 5 hours post induction using a continuous flow centrifuge (T-1-P Sharpies) and the resulting paste was stored at −70° C.

When grown in 2 L baffled shake flasks, a 250 ml culture containing the construct of interest was grown overnight in a 500 ml baffled shake flask in Terrific Broth (12 gm tryptone, 24 gm yeast extract, 4 ml glycerol per liter) containing 50 μg/ml carbenicillin. The next day 2 L baffled shake flasks containing 800 ml of Terrific Broth with 100 μg/ml ampicillin and 0.2% glucose were inoculated with 12 ml of the overnight culture and grown in a New Brunswick incubator shaker at 240 rpm until the $OD_{600mm}$ reached 0.8 at which time IPTG was added to a final concentration of 1.0 mM. Cultures were allowed to grow an additional 5 hours post induction. Cells were then harvested by centrifugation and stored at −70° C. At all times cultures were grown at 30° C to permit expression of bFGF in the soluble E. coli fraction.

Mutant and wild-type proteins were purified by first resuspending E. coli cell paste (stored at −70° C.) in load buffer (50 mM HEPES, pH7.5, 100 mM NaCl. 10 mM Dithiothreitol (DTT), 1 mM EDTA) to which the following protease inhibitors were added: 1 mM PMSF, 1 μg/ml pepstatin A and 1 μg/ml leupeptin. Typically, 50 gm of cell paste was resuspended in 300 ml buffer and sonicated on ice using a Branson Ultrasonics Sonifier 450 (Danbury, Conn.) until cells were completely lysed. The lysed cell suspension was then centrifuged at 4° C. in a Beckman Avanti™ J-25 centrifuge at 75,000× g for 30 min. Supernatants were combined and filtered through a 0.8 μM filter. The entire sample was then applied at 3 ml/min to a 5 ml HiTrap SP column (Pharmacia Biotech, Uppsala, Sweden) previously equilibrated with load buffer and attached to a GradiFrac System (Pharmacia Biotech, Uppsala, Sweden). Following sample load the column was washed with load buffer until the $A_{280}$ of the eluate returned to baseline. A 5 ml HiTrap Heparin was attached in tandem to the SP column and bound protein was humped from the SP column to the Heparin column using 0.6 M NaCl in load buffer. Under these conditions bFGF is eluted from the SP resin and binds specifically to the Heparin affinity column. Following an extensive wash of the HiTrap Heparin column using 0.6 M NaCl to remove non-specifically bound protein, bFGF is eluted with 0.6 M NaCl to 3.0 M NaCl linear gradient. Wild-type and mutant proteins were routinely purified to >95% using this procedure as determined by SDS-PAGE. In addition, all mutant proteins eluted at the same NaCl concentration as wild-type bFGF indicating that the mutations had not altered the affinity for heparin. We have previously reported that there is a good correlation between NaCl elution from a heparin affinity column and $K_d$ for heparin binding to bFGF measured by isothermal titration calorimetry (Thompson et al., Biochemistry 33:3831–3840 (1994)); A similar binding affinity for heparin for each of these mutants compared to the wild-type protein is also independent confirmation that no gross structural perturbations resulted due to the introduced mutation(s).

Protein concentrations were determined by measuring the absorbance at 280 nm and using an extinction coefficient of 16,766 $M^{-1}$ $cm^{-1}$ as reported by Pantoliano et al., Biochemistry 33:10229–10248 (1994)). For mutations in which an additional tyrosine was introduced upon site-directed mutation the extinction coefficient was calculated by addition of the individual extinction coefficients for tryptophans and tyrosines.

Example 3 bFGF Mutein Mitogenicity

In order to demonstrate superagonist, mitogenic activity of the bFGF mutant proteins, experiments were undertaken to directly compare mutein and wild-type bFGF stimulation of fibroblast growth. NIH 3T3 mouse embryo fibroblast (1658-CRL), 3T3 Swiss albino mouse fibroblast ($CCL_1$-92) and Balb/c 3T3 clone A31 mouse embryo fibroblast (9163-CCL) cell lines were obtained from the ATCC (American Type Culture Collection, Rockville, Md.). Cells were maintained in T-75 or T-150 tissue culture flash in Dulbecco's modified Eagle's media (DMEM) containing L-Glutamine, low glucose, 110 mg/l sodium pyruvate, pyridoxine hydrochloride and supplemented with 10% (v/v) heat-inactivated calf serum (Gibco, Grand Island, N.Y.) For assays, the cell were seeded in 96 well plates in Dulbecco's modified Eagle's medium nutrient mixture F12 Ham (DMEM/F12 1:1 mixture) containing L-glutamine, 15 mM Hepes, sodium bicarbonate, and lacking phenol red (Sigma, St. Louis, Mo.) supplemented with 0.5% or 1.0% (v/v) calf serum.

Promotion of cell proliferation for the various fibroblast cell lines was determined using the CellTiter96® AQUeous Non-Radioactive Cell Proliferation Assay (Promega, Madison, Wis.). This assay relies on mitochondrial dehydrogenase enzymes to reduce a soluble tetrazolium compound into formazan in the presence of an electron coupling reagent (Dunigan et. al., Biotechniques 19:640–649 (995)). The quantity of formazan product is directly proportional to the number of viable cells in culture and is easily monitored at an absorbance of 490 nm. This method has been shown to be equivalent to other methods of quantitating cell proliferation (Gicni et al., Immun. Methods J. 187:85–93 (1995); Roehm et al., Immun. Methods J. 142: 257–265 (1991); Drummond et al., Biochem. Biophys. Methods J. 31:123–134(1996)).

Assays were performed in 96 well plates according to the manufacturer's protocol (Promega, Technical Bulletin #169) using either Falcon #3072 or Costar #3596 low evaporation lid tissue culture plates (Fisher Scientific. Pittsburgh, Pa.). Dilutions (typically ranging from 100 to 0.001 ng/ml) of wild-type and site-directed mutant bFGFs to be assayed were made serially in 96 well plates using low serum media and then warmed to 37° C. Fibroblast cells were detached from T-150 plates by use of 0.25% trypsin (Gibco, Grand Island, N.Y.) for 3 minutes. Trypsin was inactivated by addition of DMEM supplemented with 10% calf serum and resting for 1 hr. Cells were then washed twice with low serum media, counted, and plated at a density of $5 \times 10^3$ cells/well into the 96-well plates containing dilutions of bFGF. Cells were incubated in the presence of bFGFs for 18–20 h at 37° C. under 5% $CO_2$ and plates were processed according to the manufacturer's recommendations. Absorbance was measured at 490 nm (nimus 700 nm to correct for background) Using a SPECTRAmax™ 250 Microplate Spectrophotometer (Molecular Devices, Sunnyvale Calif.). Each dilution was run in quadruplicate and all plates had a negative control also in quadruplicate (cells in low serum medium with no added growth factor) which was subtracted from the mean of each quadruplicate value.

Figure 2:
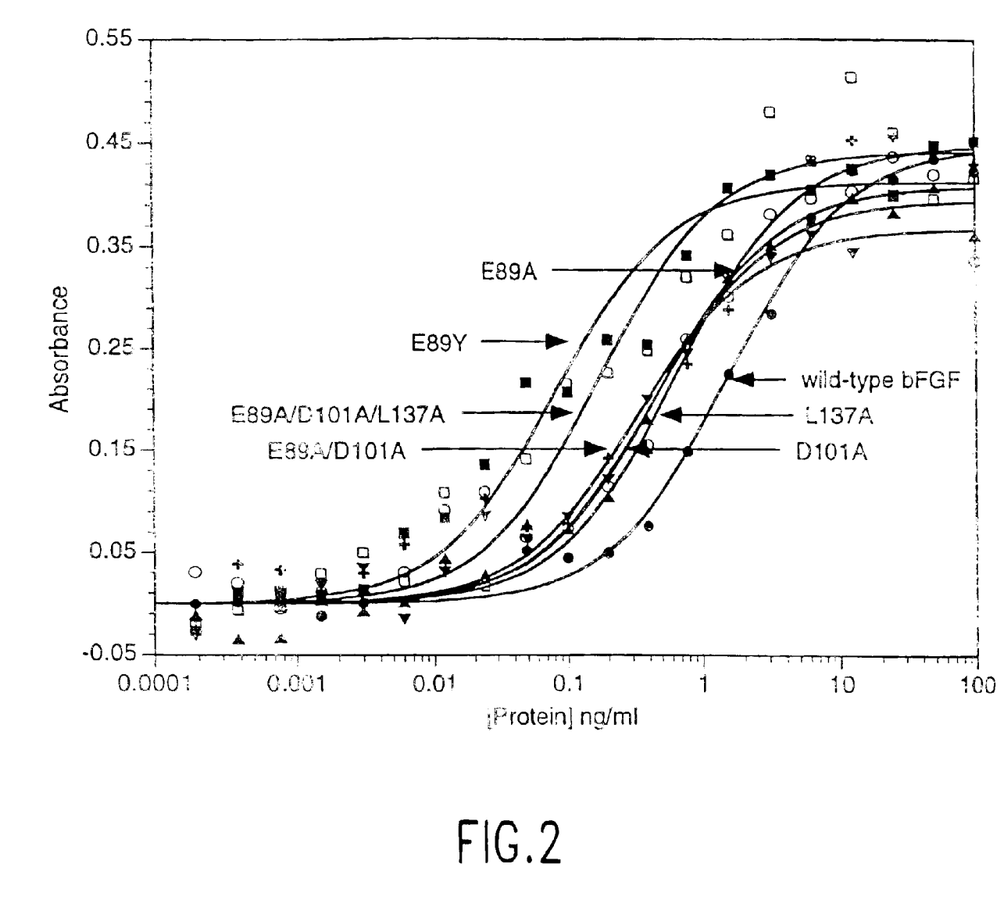
FIG. 2. This figure displays the results of a single mitogenicity experiment in which the wild-type and mutant bFGFs were all assayed simultaneously on Swiss 3T3 fibroblasts and is representative of the data compiled in Table I.

An exemplary experiment is presented in FIG. 2, demonstrating the lower $ED_{50}$ values of the bFGF muteins. Data from experiments similar to what is presented in FIG. 2 were utilized to construct Table 1. Mutant designations are as described in the detailed description of FIG. 2, and $ED_{50}$ is defined as the concentration of growth factor required to achieve ½ maximal stimulation of a defined cell line.

Belong in Table 1, superagonist mitogenicity of the bFGF muteins is demonstrated. Mutein $ED_{50}$ values are reported as ratios to wild-type bFGF to compensate for assay to assay variation and to provide a measure of bFGF mutein mitogenicity relative to wild-type bFGF. Values reported were obtained utilizing recombinant wild-type bFGF expressed and purified from *E. coli* and mutant forms of bFGF expressed and purified in an identical manner to the wild-type protein. Values reflect X-fold enhanced activity over the wild-type protein (X=the ratio reported in the Table 1), n refers to the number of experiments performed. For all mutant bFGF data reported in Table 1, three fibroblast cell lines were used (Swiss 3T3, NIH 3T3 and Balb/c 3T3). Although the absolute $ED_{50}$ values varied for wild-type bFGF and muteins, the ratio of wild-type $ED_{50}$/mutant $ED_{50}$ remained consistent for the three cell lines tested.

TABLE 1

Mitogenic Activity of bFGF Superagonists

| Mutant bFGF | Wild-type bFGF $ED_{50}$/ Mutant bFGF $ED_{50}$ | n (number of experiments) - |
|---|---|---|
| E89A | 2.8 | 42 |
| E89Y | 13.0 | 40 |
| D101A | 4.4 | 26 |
| E89A, D101A | 14.3 | 10 |
| E89A, D101A, L137A | 7.3 | 12 |
| L137A | 2.5 | 25 |

As is evidenced in the data presented in FIG. 2 and Table 1, all of the mutant bFGF proteins are significantly more mitogenic than the wild-type bFGF protein.

What is claimed is:

1. A mutein of human basic fibroblast growth factor, or a biologically active peptide thereof, comprising the substitution of a neutral and/or hydrophobic amino acid for one or more of the following:
   (a) Glutamate 89; or
   (b) Aspartate 101; or
   (c) Leucine 137.

2. The mutein of claim 1 which comprises the substitution of a hydrophobic amino acid for $Glu^{89}$.

3. The mutein of claim 1 which comprises the substitution of a hydrophobic amino acid for $Asp^{101}$.

4. The mutein of claim 1 which comprises the substitution of a hydrophobic amino acid for $Leu^{137}$.

5. The mutein of claim 1 which comprises the substitution of a neutral amino acid for $Glu^{89}$.

6. The mutein of claim 1 which comprises the substitution of a neutral amino acid for $Asp^{101}$.

7. The mutein of claim 1 which comprises the substitution of a neutral amino acid for $Leu^{137}$.

8. The mutein of claim 1 wherein a neutral amino acid is defined as alanine and a hydrophobic amino acid is defined as tyrosine.

9. The mutein of claim 1 which is human basic fibroblast growth factor $[Tyr^{101}]$.

10. The mutein of claim 1 which is human basic fibroblast growth factor $[Tyr^{137}]$.

11. The mutein of claim 1 which is human basic fibroblast growth factor $[Tyr^{89, 101}]$.

12. The mutein of claim 1 which is human basic fibroblast growth factor $[Tyr^{89, 137}]$.

13. The mutein of claim 1 which is human basic fibroblast growth factor $[Tyr^{101, 137}]$.

14. The mutein of claim 1 which is human basic fibroblast growth factor $[Tyr^{89, 101, 137}]$.

15. A polynucleotide encoding the mutein of claim 1.

16. The polynucleotide of claim 15 which is DNA.

17. The polynucleotide of claim 15 which is a cDNA.

18. A vector containing the DNA of claim 17.

19. A host cell comprising the vector of claim 18.

20. A process for producing a polypeptide comprising expressing from the host cell of claim 19 the polypeptide encoded by said DNA.

21. A process for producing the vector of claim 18 which comprises:
   (a) inserting the polynucleotide of claim 17 into the vector; and
   (b) selecting and propagating said vector in a host cell.

22. The polynucleotide of claim 15 which is RNA.

23. A vector containing the RNA of claim 22.

24. A host cell comprising the vector of claim 23.

25. A process for producing a polypeptide comprising expressing from the host cell of claim 24 the polypeptide encoded by said DNA.

26. A process for producing the vector of claim 23 which comprises:
   (a) creating a recombinant RNA molecule containing the RNA sequence of claim 22; and
   (b) selecting and propagating said vector in a host cell.

27. The polynucleotide of claim 15, wherein said neutral amino acid is selected from the group consisting of serine, threonine, alanine, asparagine, glutamine, cysteine, glycine and histidine, and said hydrophobic amino acid is selected from the group consisting of tyrosine, leucine, isoleucine, valine, proline, phenylalanine, tryptophan, and methionine.

28. The mutein of claim 1, wherein said neutral amino acid is selected from the group consisting of serine, threonine, alanine, asparagine, glutamine, cysteine, glycine and histidine, and said hydrophobic amino acid is selected from the group consisting of tyrosine, leucine, isoleucine, valine, proline, phenylalanine, tryptophan, and methionine.

29. A pharmacologic composition useful for stimulating cell division comprising the following:
   (a) An effective amount of the human basic fibroblast growth factor mutein of claim 1; and
   (b) An acceptable pharmaceutical carrier.

* * * * *

UNITED STATES PATENT AND TRADEMARK OFFICE
CERTIFICATE OF CORRECTION

PATENT NO.    : 6,767,722 B1
DATED         : July 27, 2004
INVENTOR(S)   : Springer et al.

It is certified that error appears in the above-identified patent and that said Letters Patent is hereby corrected as shown below:

Column 2,
Line 40, delete "26879-2688" and replace with -- 26879-26884 --.

Column 20,
Line 39, delete "(995)" and replace with -- (1995) --.
Line 45, delete "Gicni" and replace with -- Gieni --.

Signed and Sealed this

Eighteenth Day of January, 2005

JON W. DUDAS
*Director of the United States Patent and Trademark Office*

SEQUENCE LISTING

```
<160> NUMBER OF SEQ ID NOS: 4

<210> SEQ ID NO 1
<211> LENGTH: 483
<212> TYPE: DNA
<213> ORGANISM: Homo sapiens
<220> FEATURE:
<221> NAME/KEY: CDS
<222> LOCATION: (1)..(474)
<223> OTHER INFORMATION:
<220> FEATURE:
<221> NAME/KEY: mat_peptide
<222> LOCATION: (4)..()
<223> OTHER INFORMATION:

<400> SEQUENCE: 1 atg ggc acc atg gca gcc ggg agc atc acc acg ctg ccc gcc ctt ccg      48
Met Gly Thr Met Ala Ala Gly Ser Ile Thr Thr Leu Pro Ala Leu Pro
 -1  1               5                  10                  15 gag gat ggc ggc agc ggc gcc ttc ccg ccc ggg cac ttc aag gac ccc      96
Glu Asp Gly Gly Ser Gly Ala Phe Pro Pro Gly His Phe Lys Asp Pro
              20                  25                  30 aag cgg ctg tac tgc aaa aac ggg ggc ttc ttc ctg cgc atc cac ccc     144
Lys Arg Leu Tyr Cys Lys Asn Gly Gly Phe Phe Leu Arg Ile His Pro
          35                  40                  45 gac ggc cga gtt gac ggg gtc cgg gag aag agc gac cct cac atc aag     192
Asp Gly Arg Val Asp Gly Val Arg Glu Lys Ser Asp Pro His Ile Lys
      50                  55                  60 cta caa ctt caa gca gaa gag aga gga gtt gtg tct atc aaa gga gtg     240
Leu Gln Leu Gln Ala Glu Glu Arg Gly Val Val Ser Ile Lys Gly Val
  65                  70                  75 tgt gct aac cgg tac ctg gct atg aaa gaa gat ggt cga ctg ctg gct     288
Cys Ala Asn Arg Tyr Leu Ala Met Lys Glu Asp Gly Arg Leu Leu Ala
 80                  85                  90                  95 tct aaa tgc gtt acc gat gag tgc ttc ttc ttc gaa cgt ctc gag tct     336
Ser Lys Cys Val Thr Asp Glu Cys Phe Phe Phe Glu Arg Leu Glu Ser
                 100                 105                 110 aac aac tac aac acc tac cgt tcg aga aaa tac acc agt tgg tat gtg     384
```

```
                                                      -continued

Asn Asn Tyr Asn Thr Tyr Arg Ser Arg Lys Tyr Thr Ser Trp Tyr Val
            115                 120                 125 gca ctt aag cgt acc ggt cag tac aaa ctt ggt tct aag acg ggc cca       432
Ala Leu Lys Arg Thr Gly Gln Tyr Lys Leu Gly Ser Lys Thr Gly Pro
        130                 135                 140 ggt cag aaa gct atc ctg ttc ctg ccg atg tct gct aaa tct tgaggatcc     483
Gly Gln Lys Ala Ile Leu Phe Leu Pro Met Ser Ala Lys Ser
    145                 150                 155

<210> SEQ ID NO 2
<211> LENGTH: 158
<212> TYPE: PRT
<213> ORGANISM: Homo sapiens

<400> SEQUENCE: 2

Met Gly Thr Met Ala Ala Gly Ser Ile Thr Thr Leu Pro Ala Leu Pro
-1  1               5                   10                  15

Glu Asp Gly Gly Ser Gly Ala Phe Pro Pro Gly His Phe Lys Asp Pro
                20                  25                  30

Lys Arg Leu Tyr Cys Lys Asn Gly Gly Phe Phe Leu Arg Ile His Pro
            35                  40                  45

Asp Gly Arg Val Asp Gly Val Arg Glu Lys Ser Asp Pro His Ile Lys
        50                  55                  60

Leu Gln Leu Gln Ala Glu Glu Arg Gly Val Val Ser Ile Lys Gly Val
    65                  70                  75

Cys Ala Asn Arg Tyr Leu Ala Met Lys Glu Asp Gly Arg Leu Leu Ala
80                  85                  90                  95

Ser Lys Cys Val Thr Asp Glu Cys Phe Phe Phe Glu Arg Leu Glu Ser
                100                 105                 110

Asn Asn Tyr Asn Thr Tyr Arg Ser Arg Lys Tyr Thr Ser Trp Tyr Val
            115                 120                 125

Ala Leu Lys Arg Thr Gly Gln Tyr Lys Leu Gly Ser Lys Thr Gly Pro
        130                 135                 140

Gly Gln Lys Ala Ile Leu Phe Leu Pro Met Ser Ala Lys Ser
    145                 150                 155

<210> SEQ ID NO 3
<211> LENGTH: 175
<212> TYPE: DNA
<213> ORGANISM: Homo sapiens

<400> SEQUENCE: 3
ctggctatga aggaagatgg aagattactg gcttctaaat gtgttacgga tgagtgtttc     60 tttttgaac gattggaatc taataactac aatacttacc gctcgagaaa atacaccagt     120
tggtatgtgg cacttaagcg taccggtcag tacaagcttg gttctaaaac gggcc          175

<210> SEQ ID NO 4
<211> LENGTH: 11
<212> TYPE: PRT
<213> ORGANISM: Artificial Sequence
<220> FEATURE:
<221> NAME/KEY: misc_feature
<223> OTHER INFORMATION: T7 peptide

<400> SEQUENCE: 4

Met Ala Ser Met Thr Gly Gly Gln Gln Met Gly
1               5                   10
```